United States Patent
Chrysanthakopoulos et al.

(10) Patent No.: US 12,115,810 B2
(45) Date of Patent: Oct. 15, 2024

(54) WRITING INSTRUMENT

(71) Applicant: BIC Violex Single Member S.A., Anoixi (GR)

(72) Inventors: Nikolaos Chrysanthakopoulos, Anoixi (GR); Ion-Ioannis Antonakis, Anoixi (GR)

(73) Assignee: BIC Violex Single Member S.A., Anoixi (GR)

( * ) Notice: Subject to any disclaimer, the term of this patent is extended or adjusted under 35 U.S.C. 154(b) by 0 days.

(21) Appl. No.: 18/480,115

(22) Filed: Oct. 3, 2023

(65) Prior Publication Data
US 2024/0116306 A1    Apr. 11, 2024

(30) Foreign Application Priority Data
Oct. 7, 2022 (EP) ................................. 22200184

(51) Int. Cl.
    *B43K 29/08*      (2006.01)
    *A61B 5/01*      (2006.01)
    *F25B 21/02*      (2006.01)

(52) U.S. Cl.
    CPC ............. *B43K 29/08* (2013.01); *A61B 5/01* (2013.01); *F25B 21/02* (2013.01)

(58) Field of Classification Search
    CPC ...... B43K 29/08; B43K 29/00; B43K 29/007; A61B 5/01; A61B 5/015; F25B 21/02

(Continued)

(56) References Cited

U.S. PATENT DOCUMENTS

| | | | |
|---|---|---|---|
| 10,172,542 B2 * | 1/2019 | Kawaguchi | ........ A61B 5/1124 |
| 2013/0060124 A1 | 3/2013 | Zietsma | |

FOREIGN PATENT DOCUMENTS

| | | |
|---|---|---|
| CN | 205033776 U | 2/2016 |
| JP | 5202734 B2 | 6/2013 |

OTHER PUBLICATIONS

Nohara, K., Sekiwa, S., Sato, M., Yamaguchi, T., & Harada, T. (2021). Development of a Pen-Type Device for SPIDAR-Tablet that Presents Force and Thermal Sensations. In C. Stephanidis, M. Kurosu, J. Y. C. Chen, G. Fragomeni, N. Streitz, S. Konomi, H. Degen, & S. Ntoa (Eds.), HCI International 2021. (Year: 2021).*

(Continued)

*Primary Examiner* — David J Walczak
(74) *Attorney, Agent, or Firm* — Bookoff McAndrews, PLLC

(57) ABSTRACT

A measuring recovery of a finger skin temperature of a writing instrument's user, comprising: measuring a first finger skin temperature of a user's finger contacting a grip area of the writing instrument during a writing session with the writing instrument; cooling the finger contacting the grip area with a cooling element and for a cooling duration; measuring a second finger skin temperature after lapse of the cooling duration; calculating the skin temperature reduction; measuring a series of finger temperature measurements after lapse of the cooling duration; calculating a temperature recovery rate based on the series of finger temperature measurements; comparing the skin temperature reduction and the temperature recovery rate to historical data and/or reference data; and providing an indication to the user in case that the skin temperature reduction and/or the temperature recovery rate are abnormal as compared to the historical data and/or reference data.

19 Claims, 4 Drawing Sheets

(58) Field of Classification Search
USPC .......................................................... 401/195
See application file for complete search history.

(56) References Cited

OTHER PUBLICATIONS

Anbalagan B, Karnam Anantha S, Arjunan SP, Balasubramanian V, Murugesan M, R K. A Non-Invasive IR Sensor Technique to Differentiate Parkinson's Disease from Other Neurological Disorders Using Autonomic Dysfunction as Diagnostic Criterion. Sensors. 2022; 22(1):266. https://doi.org/10.3390/s22010266.
European Search Report issued in European Application No. 22200184, mailed on Mar. 10, 2023.

* cited by examiner

WRITING INSTRUMENT

CROSS REFERENCE TO RELATED APPLICATIONS

This application claims benefit from European patent application EP 22200184.4 filed on 7 Oct. 2022, its content being incorporated herein by reference.

TECHNICAL FIELD

The present disclosure relates to a method for measuring recovery of a finger skin temperature of a writing instrument's user and a writing instrument for measuring recovery of a finger skin temperature of its user.

BACKGROUND

Parkinson's disease (PD) is a long-term degenerative disorder of the central nervous system that mainly affects the motor system. The cause of PD is unknown, with both inherited and environmental factors believed to play a role.

The symptoms are due to the death of cells in the substantia nigra, a region of the midbrain, leading to a dopamine deficit. The cause of this cell death is poorly understood but involves the build-up of misfolded proteins into Lewy bodies in the neurons.

Its general symptoms include tremor, loss of smell, trouble sleeping, trouble moving or walking, constipation, a soft or low voice, masked face, dizziness or fainting, hunching over. Parkinson's disease begins to become significant for people over 50 years old.

SUMMARY

In a first general aspect, the present disclosure relates to a computer-implemented method for measuring recovery of a finger skin temperature of a writing instrument's user, comprising:
  measuring a first finger skin temperature of at least one user's finger contacting a grip area of the writing instrument during a writing session with the writing instrument;
  cooling the at least one finger contacting the grip area with a cooling element and for a cooling duration;
  measuring a second finger skin temperature after lapse of the cooling duration;
  calculating the skin temperature reduction;
  measuring a series of finger temperature measurements after lapse of the cooling duration;
  calculating a temperature recovery rate based on the series of finger temperature measurements;
  comparing the skin temperature reduction and the temperature recovery rate to historical data from the same user or to reference data from a group of users; and
  providing an indication to the user in case that the skin temperature reduction and/or the temperature recovery rate are abnormal as compared to the historical data and/or to the reference data.

In embodiments, the method may comprise storing calculated skin temperature reduction data and calculated temperature recovery rate data as historical data.

In embodiments, the method may comprise measuring at least one of ambient temperature to normalize the skin temperature measurements, cooling surface temperature to control setting of a cooling temperature, and temperature of a cooling element of the writing instrument to ensure safe operation.

In embodiments, the method may comprise dissipating heat of a cooling element of the writing instrument through two or more air venting openings of the writing instrument.

In embodiments, the skin temperature reduction and/or the temperature recovery rate may be abnormal when their values are below a specific threshold.

In a second general aspect, the present disclosure relates to a writing instrument for measuring recovery of a finger skin temperature of its user, comprising:
  one or more temperature sensors configured to measure a finger skin temperature of at least one user's finger contacting a grip area of the writing instrument during a writing session with the writing instrument;
  at least one cooling element configured to cool the at least finger contacting the grip area with a cooling temperature and a cooling duration;
  a computer system configured to execute the computer-implemented method for measuring recovery of a finger skin temperature according to one of the preceding claims; and
  a communication system configured to provide an indication to the user in case that a skin temperature reduction and/or a temperature recovery rate are abnormal as compared to historical data and/or to reference data.

In embodiments, the writing instrument may comprise a storage system configured to store calculated skin temperature reduction data and calculated temperature recovery rate data as historical data.

In embodiments, the writing instrument may comprise at least one further temperature sensor configured to measure at least one of ambient temperature, cooling surface temperature, and temperature of a cooling element of the writing instrument.

In embodiments, the writing instrument may comprise two or more air venting openings configured to dissipate heat of a cooling element of the writing instrument.

In embodiments, the writing instrument may comprise at least one microfan or micropump in fluid connection with the two or more air venting openings.

In embodiments, the cooling element may be a thermoelectric cooling element.

In embodiments, the writing instrument may comprise a heat conductive surface arranged at an outside surface of the cooling element.

In embodiments, the cooling element comprises a hole in which a temperature sensor is accommodated.

In embodiments, the temperature sensor comprises at least one of a thermocouple, a thermistor, a resistance temperature detector, and an IR temperature detector.

In embodiments, the writing instrument may comprise a user interface configured to receive input from a user and/or to provide information to the user such as the indication and/or the calculation results; and/or a wireless communication system configured to provide the indication and/or the calculation results via an external device having an interface.

According to examples of the present disclosure, indications of autonomic dysfunction related to neurodegenerative diseases like PD are obtained through the measurement of fingers skin temperature reduction and recovery of a user performing handwriting. Finger cold stress is enabled by the incorporation of thermoelectric cooling elements on the finger grip positions of a writing instrument. Skin temperature measurement is enabled by the incorporation of temperature sensors at finger grip positions of the writing instrument.

Steps of an example method of the present disclosure may be as follows:
- User holds the writing instrument with his three fingers at the grip positions.
- Temperature sensors measure finger skin temperature at normal conditions.
- His fingers are in contact with the respective thermoelectric cooling elements.
- Cooling elements are activated and set to a specific cooling temperature.
- After a preset time, cooling action stops.
- Temperature sensors start measuring finger skin temperature after cold stress for a specific time.
- System records skin temperature reduction and temperature recovery rate.
- System alerts user for the results.

An example system of the present disclosure may provide the following features:
- A smart pen with appropriate electronics and a power source capable of powering all the components with DC voltage.
- An area with thermoelectric cooling elements at the fingers gripping position of the smart pen body, permitting the cooling of the skin.

In examples, the system may comprise appropriate heat conductive elements over the thermoelectric cooling elements.

In examples, the system may comprise an area with temperature sensors adjacent, between or within the cooling elements of the smart pen.

In examples, the system may comprise an area with thermal insulating material between cooling elements and the temperature sensors, to avoid any thermal influence.

In examples, the system may comprise heat sink elements on the hot side of the TEC elements.

In examples, the system may comprise air venting openings at different locations of the pen body to dissipate heat generated by TEC element.

In examples, the system may comprise notification LED elements, microfans or micropumps to dissipate heat.

In examples, the smart pen may comprise operation buttons and network capabilities for transmitting measurement data.

In examples, the system may comprise a smartphone or tablet receiving measurement data.

In examples, the system may comprise a software application for the operation of the smart pen and the visualization of the data.

Particular examples of the first to second general aspects can be implemented so as to realize one or more of the following advantages.

In examples, the present disclosure enables to induce cold stress and measure skin temperature on the fingers of a user of a smart pen during handwriting without any user action other than holding the pen.

In examples, the present disclosure enables to measure and record skin temperature over time and identify consistent changes like e.g., maximum temperature decrease and/or a slow skin temperature recovery rate.

In examples, the present disclosure enables to correlate significant skin temperature changes to autonomic nerve disfunction or degeneration and alert the user to seek medical advice.

The present disclosure allows identifying a chronic or degenerative disease in early stages which is very difficult in most cases.

The present disclosure allows to detect the quality of handwriting which may be severely affected when medium to severe symptoms of a chronic or neurodegenerative disease are expressed.

The present disclosure overcomes issues in that testing for and measuring biomarkers related to neurodegenerative diseases is a process performed in a medical point of care (hospital, doctors office) and may require sophisticated equipment.

Regarding skin temperature as a biomarker, an autonomic dysfunction, an early symptom in PD, is caused by α-synuclein pathogenesis in the central nervous system and can be diagnosed using skin vasomotor response to cold stimuli.

During a relevant medical study infrared thermography was used for the cold stress test to observe subjects hand temperature before and after cold stimuli. To induce the cold stress, a bowl full of cold water at 3° C. was placed for the patient to immerse both hands to the wrist wrapped in a latex glove. The temperature was measured with an IR detector e.g. a FLIR T460, 320×240 60 Hz thermographic IR detector with a thermal sensitivity <0.03° C.

A reduced mean baseline temperature for the same cold stress temp was observed in PD subjects when compared to healthy subjects. It was also observed that the hand temperature recovery rate at 6 minutes after cold stress test of PD subjects was 32% less when compared to healthy subjects. These results show that this non-invasive technique can be used as an effective tool in the diagnosis and differentiation of PD in its early stage.

A skin temperature contact sensor may be a compact biomedical thermistor. The thermistor is a small, ceramic-encapsulated metal-oxide semiconductor. It exhibits a characteristic non-linear inverse relationship between resistance and temperature that allows it to be used as a temperature sensor. The relatively large change in resistance as a function of temperature (~4%/° C.) gives a signal response far greater than thermocouples and resistance temperature devices (RTD). The metal case of the probe is held flat against the skin of the subject and is usually taped into position. There are several small-scale skin temperature measurement systems developed for wearables offering ±0.1 C accuracy.

Thermoelectric cooling may use the Peltier effect to create a heat flux at the junction of two different types of materials. A Peltier cooler, heater, or thermoelectric heat pump is a solid-state active heat pump which transfers heat from one side of the device to the other, with consumption of electrical energy, depending on the direction of the current.

Such an instrument is also called a Peltier device, Peltier heat pump, solid state refrigerator, or thermoelectric cooler (TEC) and occasionally a thermoelectric battery. It can be used either for heating or for cooling, although in practice the main application is cooling. Miniature thermoelectric cooler elements are commercially available.

Regarding writing action, handwriting is the writing action done with a writing instrument, such as a pen or pencil, using the hand. Handwriting includes both printing and cursive styles. Handwriting involves the use of a pen or pencil which the user keeps holding with his hand/fingers even when he does not write. At a writing session the user writes or sketches with a writing instrument. A writing session includes actual handwriting instances and on-air instances in which a tip of the writing instrument is not touching a writing surface.

Significant changes or the deterioration of a person's handwriting may be a symptom or a result of several different diseases.

The normal pen grip may be performed in the following way:
- the writing instrument is held in a stable position between the thumb, index and middle fingers,
- the ring and little fingers are bent and rest comfortably on the table,
- the index finger and thumb form an open space,
- the wrist is bent back slightly, and the forearm is resting on the table,
- the writing instrument is held about 1-2 cm from the tip.

Certain terms are used in the following manner in the present disclosure:

The expression "digital device" may refer to an electronic device that uses discrete, numerable data and processes for all its operations, and is capable of displaying content to the user. Examples of such a device include but are not limited to: Mobile phones, Laptops, Tablets, Personal computers, Netbooks, iPads, etc.

DETAILED DESCRIPTION

Figure 1:
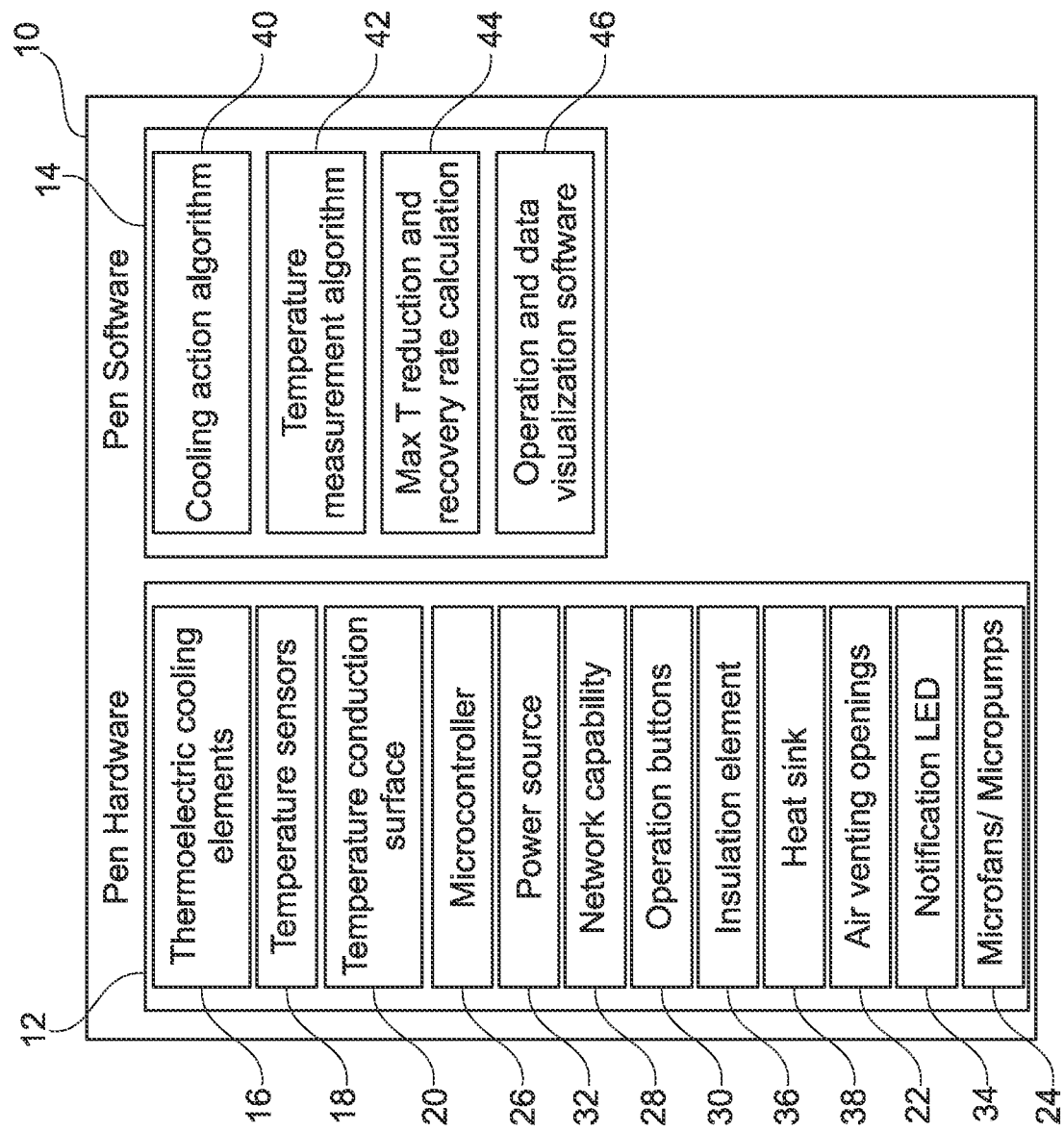
FIG. 1 illustrates an overview of components of a writing instrument for measuring recovery of a finger skin temperature of its user according to the present disclosure.

FIG. 1 shows an overview of components of a writing instrument 10 for measuring recovery of a finger skin temperature of a writing instrument's user according to the present disclosure. The writing instrument 10 can be a smart pen, a digital writing instrument or a digital device.

The writing instrument 10 includes a skin temperature recovery assessment system which is capable of measuring the skin temperature recovery rate after cold stress of the fingers of the user and evaluating if there is any abnormality.

The sweat gland innervation assessment system includes two subsystems i.e., a pen hardware or skin cold stress and temperature sensing smart pen system 12 and a pen software skin temperature changes software 14.

The skin cold stress and temperature sensing smart pen system may include the following elements:

One or more thermoelectric cooling elements 16 (TEC) capable of cooling user's fingers while holding a writing instrument 10. TEC may be located at the body of the writing instrument 10, at the lower part of the pen's body where usually a user holds the pen. The TEC elements may by located at the pen surface coming directly in contact with the skin of the user.

In examples, TEC elements may be located inside the pen body, under a heat conductive element that is located at the pen surface coming directly in contact with the skin of the user.

In embodiments, the TEC elements may be located from 0.5 cm to 7 cm from the tip of the writing instrument, more preferably from 2 cm to 5 cm.

In embodiments, the number of the TEC elements may range from 1 to 3, one for each of the fingers usually used by a user to hold a pen.

In embodiments, the width of each TEC may range from 3 mm to 20 mm.

In embodiments, the length of each TEC may range from 1 cm to 5 cm.

In embodiments, the area of each TEC may range from $0.3$ $cm^2$ to $10$ $cm^2$.

In embodiments, the TEC surface may be flat or may be curved to accommodate the shape of the writing tool.

In embodiments, the TEC elements may contain holes to accommodate the insertion of temperature sensors.

In embodiments, the TEC elements may be placed on facets of a multifaceted writing instrument. For example, there may be 3 TEC elements each one placed on a facet of a 3 faceted writing instrument, each of the facets used as the grip areas of the 3 fingers used to hold the pen to facilitate finger positioning.

In embodiments, the TEC elements cool side must be on the surface side of the smart pen's body.

In embodiments, the TEC elements hot side must be on the opposite side toward the interior of the pen's body.

In examples, one or more temperature sensors 18 may be incorporated on the smart pen.

A temperature sensor may be located at the top of the pen body to measure the environmental temperature, $T_e$. The data from the environmental T sensor are used to normalize the skin temperature measurements.

A second or more temperature sensors may be in contact with the TEC element or the heat conductive surface (at different positions) in the finger grip areas, in order to measure the cooling surface temperature, To. The data from cooling element temperature sensor are used to drive the cooling temperature setting.

A third or more temperature sensors may be located in adjacent areas or pass through the TEC elements or the heat conductive surface in order to measure the finger's skin temperature, $T_s$, before or after the application of cooling. There may be insulating materials around these temperature sensors to prevent any effect of the TEC elements cooling action.

A fourth or more temperature sensors may be located in contact with the TEC element's hot side in order to monitor the temperature and ensure that no abnormal events would cause the device to enter a thermal runaway event where the system would reach temperatures that could damage it or the user. In examples, the data from the sensor could be used to monitor the efficiency of the system.

In embodiments, the temperature sensors may be thermocouples, thermistors, resistance (RTD) or IR type.

A heat conductive surface 20 may be placed over a TEC element to facilitate cooling. The heat conductive surface may have the exact dimensions of the TEC element underneath or have a greater surface. The material of the heat conductive material may be at least one of stainless steel, Gold, Silver, Copper, Aluminium, Platinum, Tungsten, and Graphite.

Two or more air venting openings 22 may be placed on the pen body to dissipate heat, generated by the TEC element.

In embodiments, an air venting opening may be all around the circumference of the pen body.

In embodiments, it may contain several holes permitting the flow of air.

In embodiments, at least one air venting opening may be located near the pen's tip adjacent to the TEC elements.

In embodiments, a second air venting opening may be located at the top of the smart pen.

Additionally, or alternatively a single or multiple fan(s) or micropumps 24 are incorporated with dimensions appropriate to be installed in proximity to the air venting openings 22 within the assembly (miniature or microfans). Said component would ease the flow of air and ensure adequate cooling A microcontroller 26, MCU, may process and control all the sensors, circuits and functions of the smart pen and may be of conventional wearable type or may be able to perform advanced AI processing. It may contain a flash memory module. The microcontroller 26 may be a conventional ultra-low power MCU suitable for wearable applications such as but not limited a 16 or 32-bit-ARM MCU. In examples, the microcontroller 26 may be based on a platform such as customizable single-chip ASIC AI or be based on a RISC-V AI architecture. The microcontroller 26 may have a custom operating firmware.

Further, network capability 28 is included. Wireless connectivity is provided for the smart pen to interact with other devices. The network capability 28 and the other device(s) support at least one of a. Wi-Fi,
b. ANT+,
c. Bluetooth Low Energy (BLE),
d. IEEE 802.15.4.

The pen hardware 12 may further includes operation buttons 30 to control voltage and smart pen functions. The control buttons can be located on the one side or on the periphery of the smart pen.

The operation buttons 30 can be at least one of:
Touch buttons
Switches
Rotation switches
Sliding buttons The pen hardware 12 may further include a power source 32 to power electronic components of the smart pen. The power source 32 includes at least one of disposable batteries, plug-in rechargeable batteries, and a wireless inductive charging module.

The power source 32 and the associated electronic circuit is capable of delivering up to 12 V and more preferably 3 V.

The pen hardware 12 further includes at least one notification LED 34. One or more notification LED 34 may be placed on the pen's body. These are used to notify the user of the different steps of the cooling and T measurement process.

In embodiments, the notification may be achieved by different colors of the LED or by different flash patterns.

In embodiments, the visual notification may be accompanied by audio or haptic feedback signals.

In embodiments, the notification steps may include:
i. signalling of the start time of the cooling action of the TEC elements.
ii. signalling of the end time of the cooling action of the TEC elements.
iii. signalling of the start of measurement of fingers temperature after cooling.
iv. signalling of the end of measurement of fingers temperature after cooling.

The pen hardware 12 may further include at least one insulation element 36. For example, an area with thermal insulating material between cooling elements and the temperature sensors may be present to avoid any thermal influence. There may by insulating materials around these temperature sensors to prevent any effect of the TEC elements cooling action.

The pen hardware 12 may further include at least one heat sink 38. The heat sink elements may be incorporated on the hot side of the TEC elements to assist heat dissipation.

The pen software 14 may include the following elements,

A skin cooling action algorithm 40 that takes as an input the actual TEC element temperature $T_c$, the desired cooling temperature and the cooling duration, either set programmably or set manually by the user. The cooling action algorithm 40 drives the cooling action of the TEC elements 16.

In embodiments, the desired cooling temperature may range from 0° C. to 25° C. and exemplary from 5 to 10° C.

In embodiments, the cooling duration may range from 15 s to 5 min and exemplary from 30 s to 2 min.

During the cooling action, the algorithm checks through the cooling elements temperature sensor if the desired $T_c$ is achieved and maintained.

In embodiments, the algorithm may also control the notification LED signaling the start and end times of the cooling action.

In embodiments, a temperature measurement algorithm 42 takes as input the measurement of fingers temperature $T_f$, normalizes it according to environmental temperature $T_e$ and averages it over a set period of time. It measures the skin finger temperature for a set duration and it provides the data points to the calculation algorithm for the max temperature decrease and recovery rate calculation.

The temperature measurement algorithm 42, may also control the notification LED signaling the start and end times of the finger temperature measurements after cooling.

In embodiments, the temperature measurement duration may range from 1 min to 10 min, exemplary 3 min to 6 min.

In embodiments, a maximum temperature and recovery rate calculation algorithm 44 takes as input the normalized and averaged skin temperature measurements and then calculates the maximum temperature decrease and the temperature recovery rate.

The maximum temperature decrease of fingers skin temperature is calculated as the difference of the skin temperature before the start of cooling action minus the skin temperature just after the end of cooling action.

The maximum temperature decrease is compared to the historical values of the specific user or to a database of values of a similar cohort.

Depending on whether the maximum temperature decrease value is over or under a set threshold, the algorithm sends a notification signal to the visualization application characterizing the measurement as normal or abnormal.

The algorithm 44 also takes as an input the series of finger temperature measurements after cooling action, for the specific T measurement duration and calculates the rate of finger temperature recovery to the normal skin temperature.

The skin temperature recovery rate is compared to the historical values of the specific user or to a database of values of a similar cohort.

Depending on whether the skin temperature recovery rate is slower or faster than a set threshold, the algorithm 44 or an operation and data visualization software 46 sends a notification signal to the visualization application characterizing the measurement as normal or abnormal.

Additionally, or alternatively, the algorithm 44 can make use of the data from the temperature sensors that are responsible for monitoring the hot side of the TEC, to ensure that the potential thermal saturation of the heatsink is not affecting the measurements in any way. This can be considered as an on-the-fly calibration procedure.

In embodiments, the pen software 14 further includes the operation and data visualization software 46. This is a software that takes the measurements and the calculation results of the system algorithms and visualises the results to the user. It also permits the user to set specific parameters of the measurement and communicate them to the smart pen.

The above-mentioned algorithms may be executed on the writing instrument 10 or on an accompanying digital (operating) device. The operating device of the writing instrument 10 or smart pen may be a tablet, a smartphone, a smartwatch, a PC or any other suitable device capable of running the operation and visualisation application and/or the algorithms. The operating device is capable of communication wirelessly with the smart pen sending and receiving data.

In embodiments, the operating device may include, one or all the required algorithms and software for the processing and calculation of the data of the smart pen.

In embodiments, the operating device may include the user interface with which the user may interact with the smart pen and visualise the measurement results.

In embodiments, the operating device may alert the user in case of abnormal measurement data.

In embodiments, the writing instrument 10 may include a storage system configured to store calculated skin temperature reduction data and calculated temperature recovery rate data as historical data.

Figure 2:
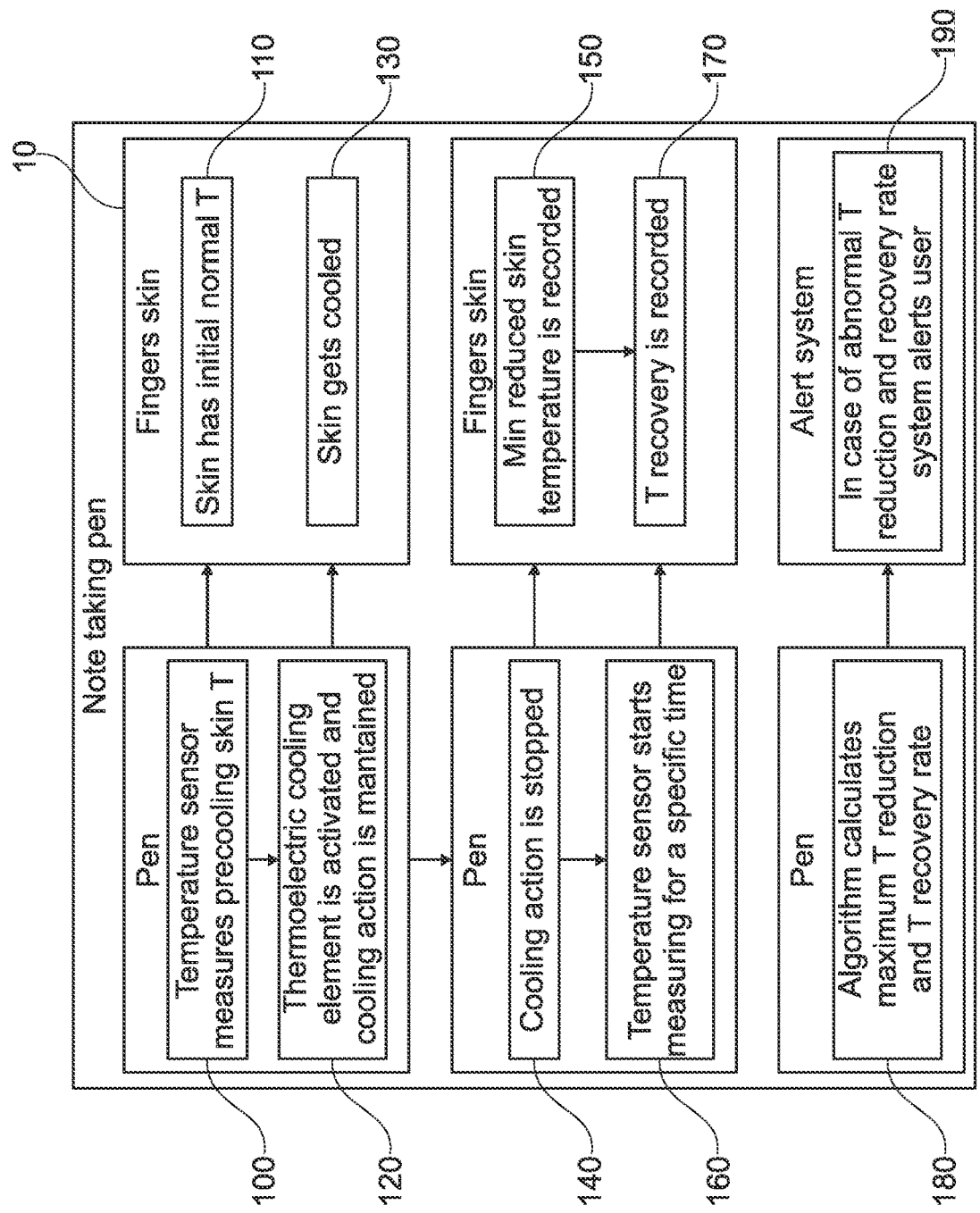
FIG. 2 illustrates a process flow diagram of a writing instrument according to the present disclosure.

FIG. 2 illustrates a process flow diagram of a writing instrument 10 according to the present disclosure. The writing instrument 10 can correspond to the writing instrument 10 as depicted in FIG. 1.

In the first step a block 100 the writing instrument 10 of pen starts to measure the first or precooling skin temperature with its temperature sensor. At a corresponding block 110, the skin has an initial normal temperature.

In block 120, the thermoelectric cooling element of the pen is activated and the cooling action is maintained. At the corresponding block 130 on the side of the user, the skin gets cooled accordingly.

At block 140, the cooling action is stopped after a predefined cooling duration. At block 150, the minimum reduced skin temperature is measured and recorded.

At block 160 the temperature sensor starts measuring for a specific time. At block 170, the corresponding recovery temperature is recorded.

At block 180, an algorithm 44 calculates the maximum temperature reduction and the temperature recovery rate. At block 190, and alert system alerts the user in case of abnormal temperature reduction and/or recovery rate. The skin temperature reduction and/or the temperature recovery rate are abnormal when their values are below a specific threshold. It could be considered abnormal when it is below 70% of the historical average values.

Figure 3:
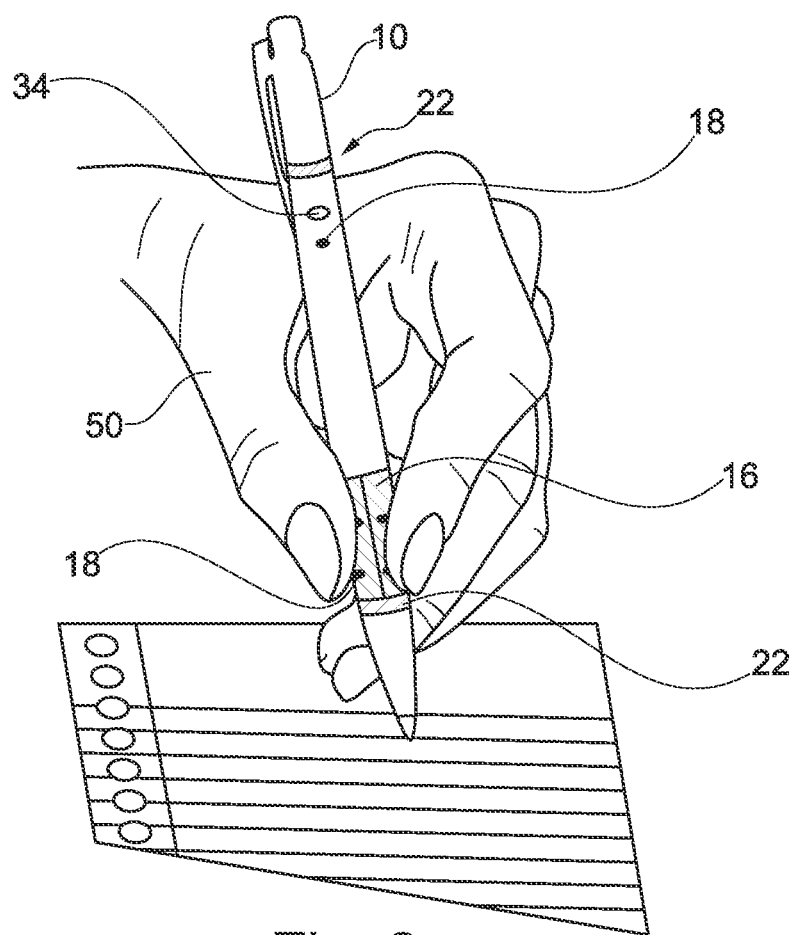
FIG. 3 illustrates a perspective view of a writing instrument according to the present disclosure.

FIG. 3 illustrates a perspective view of a writing instrument 10 according to the present disclosure. The writing instrument 10 can correspond to the writing instrument 10 as depicted in FIG. 1 and FIG. 2.

In FIG. 3, a user's hand is depicted holding the writing instrument in a typical 3 finger way.

One or more cooling elements 16 are located in a grip area of the writing instrument 10 so that at least two fingers 50 rest on the cooling element 16. At least one temperature sensor 18 is located in the grip area to measure the skin temperature of a fingertip. A further temperature sensor 18 is located in an upper portion of the writing instrument 10 opposite to the tip of the writing instrument 10. This temperature sensor 18 can measure an ambient temperature.

Two air venting openings 22 are provided on the body of the writing instrument 10. One air venting opening 22 is located close to a tip of the writing instrument e.g. between the tip and the cooling element 16. A second air venting opening 22 is located at an opposite end of the writing instrument 10. The air venting openings 22 allow for air circulation to remove heat from the writing instrument 10 which is generated by the cooling element 16.

In examples, at least one microfan or micropump in fluid connection with the two or more air venting openings 22 may be present inside the writing instrument 10 for improving the airflow.

In examples, a notification LED 34 is provided at the writing instrument 10 to inform the user about the state of the writing instrument 10 or of the cooling. The notification LED 34 may further alert the user in case of abnormal temperature reduction and/or recovery rate.

Details of the measurement are explained in conjunction with FIG. 4 below.

Figure 4:
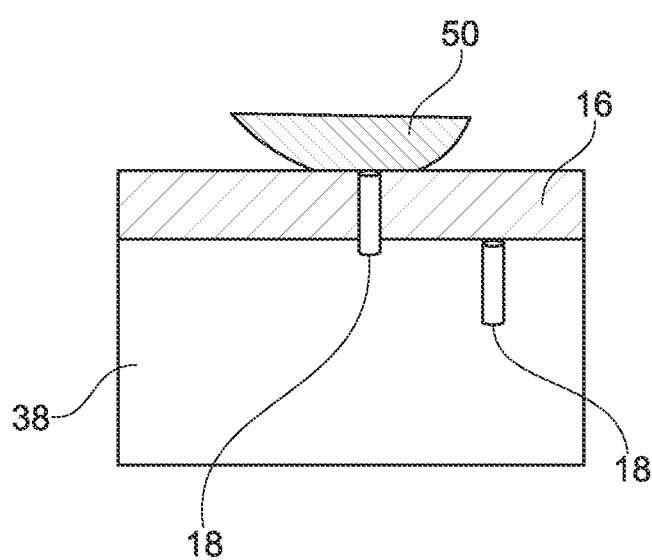
FIG. 4 illustrates a sectional view of a cooling element of a writing instrument according to the present disclosure.

FIG. 4 illustrates a sectional view of a cooling element 16 of a writing instrument 10 according to the present disclosure.

A fingertip of a finger 50 is in contact with the surface of the cooling element 16 which is for example a Peltier element. By electrically activating a cooling element 16 the fingertip 50 is cooled down.

In examples, a heat conductive surface may be arranged at an outside surface of the cooling element 16 at which the fingertip 50 rests in order to improve cooling of the fingertip.

The cooling element 16 has a hole or opening in which a temperature sensor 18 is arranged for measuring the fingertip temperature. The temperature sensor 18 is located where the user usually grips the writing instrument 10. The temperature sensor 18 may have a larger lateral extension in order to cover more gripping locations.

In examples, at a backside of the cooling element 16 a heatsink 38 is located. The heatsink 38 transports heat away from the cooling element 16 which originates from cooling action of the cooling element 16.

In examples, a further temperature sensor 18 is located at the backside of the cooling element 16 or inside or at the heat sink 38. This temperature sensor 18 measures the temperature of the cooling element 16.

Figure 5:
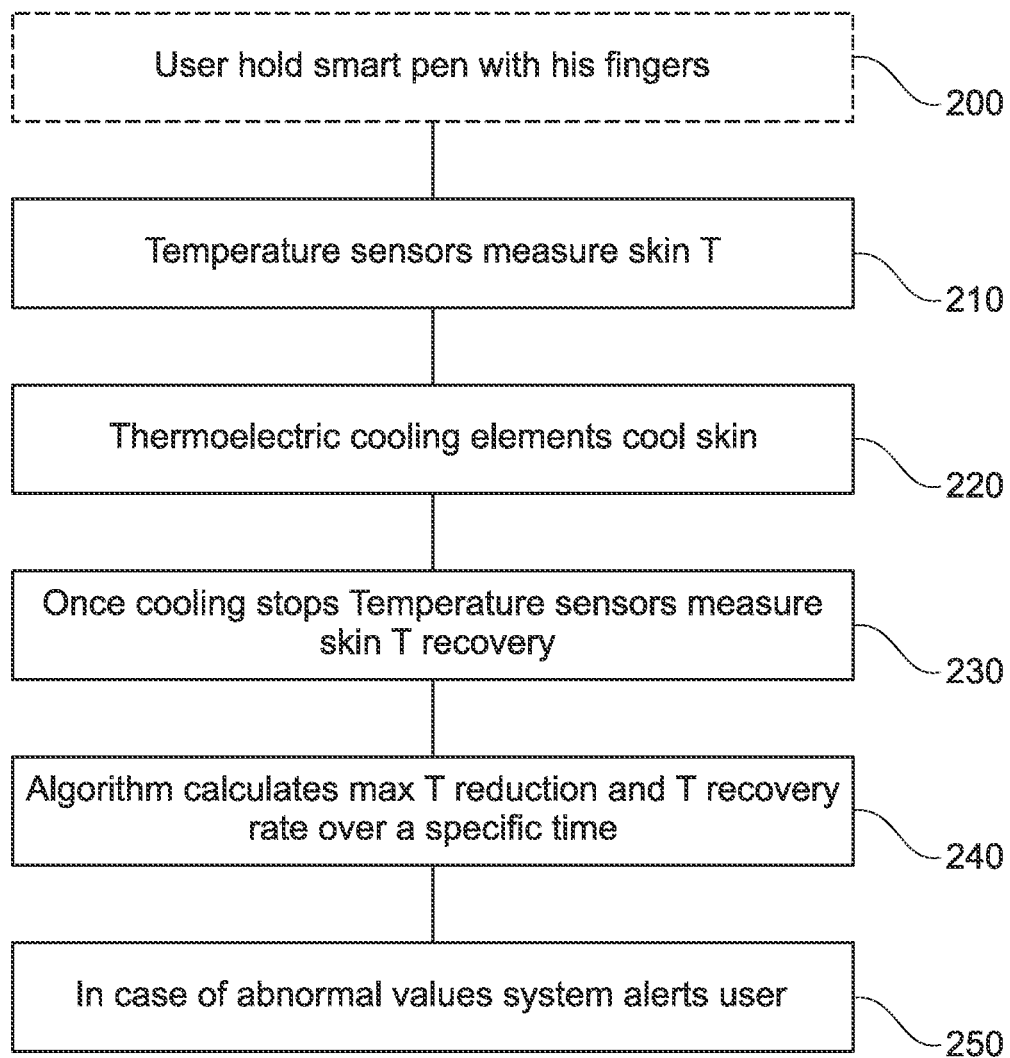
FIG. 5 illustrates a method flow chart for measuring recovery of a finger skin temperature of a writing instrument's user according to the present disclosure.

FIG. 5 illustrates a method flow chart for measuring recovery of a finger skin temperature of a writing instrument's user according to the present disclosure.

In an exemplary step 200 of the method, the user holds the smart pen or writing instrument with his fingers at the pen body grip positions.

In an exemplary step 210, the temperature sensor measures a first or initial finger skin temperature. The user may be notified to place fingers on adjacent cooling elements.

In other words, the step 210 includes measuring a first finger skin temperature of at least one user's finger contacting a grip area of the writing instrument during a writing session with the writing instrument.

In another step 220, the thermoelectric cooling elements cools the skin. The cooling elements at the finger positions are activated and get cooled until they reach a set temperature and stay at that temperature for a predetermined time. Thereby, the user's fingers get cooled through the contact with the cooling elements for a specific time duration.

In other words, the step 220 includes cooling the at least one finger contacting the grip area with a cooling element and for a cooling duration.

In another step 230, once the cooling stops the temperature sensor measures the skin temperature. The cooling elements stop cooling action and the user may be notified to place fingers on adjacent temperature sensors. The temperature sensor starts measuring finger temperature continuously for a specific time duration.

In other words, the step 230 includes measuring a second finger skin temperature after lapse of the cooling duration and measuring a series of finger temperature measurements after lapse of the cooling duration. The series measurement may include the singular measurement of measuring a second finger skin temperature after lapse of the cooling duration.

In another step 240, the algorithm calculates the maximum temperature reduction and temperature recovery rate over a specific time. This includes that an algorithm compares the measurement values with historical data of the same user or to a database of similar cohort.

In other words, the step 240 includes calculating the skin temperature reduction based on a first temperature measurement after lapse of the cooling duration and calculating a temperature recovery rate based on the series of finger temperature measurements. The step further may further include comparing the skin temperature reduction and the temperature recovery rate to historical data from the same user or to reference data from a group of users.

In another step 250, in case of abnormal values the system alerts the user. Abnormal values are lower than a specific threshold e.g., below 70% of the historical average values.

In other words, the step 250 includes providing an indication to the user in case that the skin temperature reduction and/or the temperature recovery rate are abnormal as compared to the historical data and/or to the reference data.

The steps 100 to 190 as depicted in FIG. 2 can be included in the method of FIG. 5.

The present disclosure also relates to the computer-implemented method for measuring recovery of a finger skin temperature of a writing instrument's user and the writing instrument for measuring recovery of a finger skin temperature of its user of the following aspects:

1. A computer-implemented method for measuring recovery of a finger skin temperature of a writing instrument's user, comprising:
   measuring a first finger skin temperature of at least one user's finger contacting a grip area of the writing instrument during a writing session with the writing instrument;
   cooling the at least one finger contacting the grip area with a cooling element and for a cooling duration;
   measuring a second finger skin temperature after lapse of the cooling duration;
   calculating the skin temperature reduction;
   measuring a series of finger temperature measurements after lapse of the cooling duration;
   calculating a temperature recovery rate based on the series of finger temperature measurements;
   comparing the skin temperature reduction and the temperature recovery rate to historical data from the same user or to reference data from a group of users; and
   providing an indication to the user in case that the skin temperature reduction and/or the temperature recovery rate are abnormal as compared to the historical data and/or to the reference data.

2. The method of aspect 1, comprising:
   storing calculated skin temperature reduction data and calculated temperature recovery rate data as historical data.

3. The method of one of the preceding aspects, comprising:
   measuring at least one of ambient temperature to normalize the skin temperature measurements, cooling surface temperature to control setting of a cooling temperature, and temperature of a cooling element of the writing instrument to ensure safe operation.

4. The method of one of the preceding aspects, comprising:
   dissipating heat of a cooling element of the writing instrument through two or more air venting openings of the writing instrument.

5. The method of one of the preceding aspects, wherein the cooling temperature is in the range from 0° C. to 25° C., exemplary from 5° to 10° C.

6. The method of one of the preceding aspects, wherein the cooling duration is in the range from 15 seconds to 5 minutes, exemplary from 30 seconds to 2 minutes.

7. The method of one of the preceding aspects, wherein the skin temperature reduction and/or the temperature recovery rate are abnormal when their values are below a specific threshold.

8. The method of one of the preceding aspects, wherein the indication is provided via a user interface of the writing instrument.

9. The method of one of the preceding aspects, wherein the indication is provided via a wireless communication system to an external device having an interface.

10. A writing instrument for measuring recovery of a finger skin temperature of its user, comprising:
    one or more temperature sensors configured to measure a finger skin temperature of at least one user's finger contacting a grip area of the writing instrument during a writing session with the writing instrument;
    at least one cooling element configured to cool the at least finger contacting the grip area with a cooling temperature and a cooling duration;
    a computer system configured to execute the computer-implemented method for measuring recovery of a finger skin temperature according to one of the preceding aspects; and
    a communication system configured to provide an indication to the user in case that a skin temperature reduction and/or a temperature recovery rate are abnormal as compared to historical data and/or to reference data.

11. The writing instrument of aspect 10, comprising:
    a storage system configured to store calculated skin temperature reduction data and calculated temperature recovery rate data as historical data.

12. The writing instrument of aspect 10, comprising:
    at least one further temperature sensor configured to measure at least one of ambient temperature, cooling surface temperature, and temperature of a cooling element of the writing instrument.

13. The writing instrument of one of aspects 10 to 12, comprising:
    two or more air venting openings configured to dissipate heat of a cooling element of the writing instrument.

14. The writing instrument of aspect 13, comprising:
    at least one microfan or micropump in fluid connection with the two or more air venting openings.

15. The writing instrument of one of aspects 10 to 14, wherein the cooling element is a thermoelectric cooling element.

16. The writing instrument of one of aspects 10 to 15, comprising:

a heat conductive surface arranged at an outside surface of the cooling element.

17. The writing instrument of one of aspects 10 to 16, wherein the cooling element comprises a hole in which a temperature sensor is accommodated.

18. The writing instrument of one of aspects 10 to 17, wherein the temperature sensor comprises at least one of a thermocouple, a thermistor, a resistance temperature detector, and an IR temperature detector.

19. The writing instrument of one of aspects 10 to 18, comprising:
- a user interface configured to receive input from a user and/or to provide information to the user such as the indication and/or the calculation results; and/or
- a wireless communication system configured to provide the indication and/or the calculation results via an external device having an interface.

The invention claimed is:

1. A computer-implemented method for measuring recovery of a finger skin temperature of a writing instrument's user, comprising:
   - measuring a first finger skin temperature of at least one user's finger contacting a grip area of the writing instrument during a writing session with the writing instrument;
   - cooling the at least one finger contacting the grip area with a cooling element and for a cooling duration;
   - measuring a second finger skin temperature after lapse of the cooling duration;
   - calculating the skin temperature reduction;
   - measuring a series of finger temperature measurements after lapse of the cooling duration;
   - calculating a temperature recovery rate based on the series of finger temperature measurements;
   - comparing the skin temperature reduction and the temperature recovery rate to historical data from the same user or to reference data from a group of users; and
   - providing an indication to the user in case that the skin temperature reduction and/or the temperature recovery rate are abnormal as compared to the historical data and/or to the reference data.

2. The method of claim 1, comprising:
   - storing calculated skin temperature reduction data and calculated temperature recovery rate data as historical data.

3. The method of claim 1, comprising:
   - measuring at least one of ambient temperature to normalize the skin temperature measurements, cooling surface temperature to control setting of a cooling temperature, and temperature of a cooling element of the writing instrument to ensure safe operation.

4. The method of claim 1, comprising:
   - dissipating heat of a cooling element of the writing instrument through two or more air venting openings of the writing instrument.

5. The method of claim 1, wherein the cooling temperature is in the range from 0° C. to 25° C.

6. The method of claim 1, wherein the cooling duration is in the range from 15 seconds to 5 minutes.

7. The method of claim 1, wherein the skin temperature reduction and/or the temperature recovery rate are abnormal when their values are below a specific threshold.

8. The method of claim 1, wherein the indication is provided via a user interface of the writing instrument.

9. The method of claim 1, wherein the indication is provided via a wireless communication system to an external device having an interface.

10. A writing instrument for measuring recovery of a finger skin temperature of its user, comprising:
    - one or more temperature sensors configured to measure a finger skin temperature of at least one user's finger contacting a grip area of the writing instrument during a writing session with the writing instrument;
    - at least one cooling element configured to cool the at least finger contacting the grip area with a cooling temperature and a cooling duration;
    - a computer system configured to execute the computer-implemented method for measuring recovery of a finger skin temperature according to one of the preceding claims; and
    - a communication system configured to provide an indication to the user in case that a skin temperature reduction and/or a temperature recovery rate are abnormal as compared to historical data and/or to reference data.

11. The writing instrument of claim 10, comprising:
    - a storage system configured to store calculated skin temperature reduction data and calculated temperature recovery rate data as historical data.

12. The writing instrument of claim 10, comprising:
    - at least one further temperature sensor configured to measure at least one of ambient temperature, cooling surface temperature, and temperature of a cooling element of the writing instrument.

13. The writing instrument of claim 10, comprising:
    - one or more air venting openings configured to dissipate heat of a cooling element of the writing instrument.

14. The writing instrument of claim 13, comprising:
    - at least one microfan or micropump in fluid connection with the one or more air venting openings.

15. The writing instrument of claim 10, wherein the cooling element is a thermoelectric cooling element.

16. The writing instrument of claim 10, comprising:
    - a heat conductive surface arranged at an outside surface of the cooling element.

17. The writing instrument of claim 10, wherein the cooling element comprises a hole in which a temperature sensor is accommodated.

18. The writing instrument of claim 10, wherein the temperature sensor comprises at least one of a thermocouple, a thermistor, a resistance temperature detector, and an IR temperature detector.

19. The writing instrument of claim 10, comprising:
    - a user interface configured to receive input from a user and/or to provide information to the user such as the indication and/or the calculation results; and/or
    - a wireless communication system configured to provide the indication and/or the calculation results via an external device having an interface.

* * * * *